United States Patent [19]

Robinson et al.

[11] Patent Number: 4,735,795
[45] Date of Patent: Apr. 5, 1988

[54] ALKYLAMMONIUM COMPLEXES OF DIATRIZOIC ACID AS X-RAY CONTRAST AGENTS

[75] Inventors: Malcolm L. Robinson, South Wirral; Frank Ridgway, Noctorum; Peter Timmins, Wirral, all of United Kingdom

[73] Assignee: E. R. Squibb & Sons, Inc., Princeton, N.J.

[21] Appl. No.: 648,195

[22] Filed: Sep. 7, 1984

[30] Foreign Application Priority Data

Mar. 30, 1984 [GB] United Kingdom ............... 8408250

[51] Int. Cl.$^4$ .................. A61K 49/04; C07C 63/68
[52] U.S. Cl. ............................. 424/5; 260/501.16; 424/4; 562/456
[58] Field of Search ............... 260/501.16; 562/451.1; 424/5, 4

[56] References Cited

U.S. PATENT DOCUMENTS

| | | | |
|---|---|---|---|
| 3,128,301 | 4/1964 | Larsen et al. | 424/5 |
| 3,852,341 | 12/1974 | Björk et al. | 424/5 |
| 4,018,783 | 4/1977 | Soulal et al. | 424/5 |
| 4,132,731 | 1/1979 | Klieger et al. | 424/5 |
| 4,192,859 | 3/1980 | Mackaness et al. | 424/5 |
| 4,279,887 | 7/1981 | Baldwin et al. | 424/1.1 |

FOREIGN PATENT DOCUMENTS 866184  4/1961  United Kingdom ............... 424/5

OTHER PUBLICATIONS

*Chemical Abstract*, vol. 95, No. 138626b, 1981, Baldeschweiler et al, "Lipid Vesicles Bearing Carbohydrate Surfaces as Lymphatic Directed Vehicles".

*Chemical Abstract*, vol. 96, No. 40893g, 1981, Weder et al, "Bilayer-Vesicles, Their Use and Dialysis Installation".

Havron et al, "Radiopaque Liposomes: A Promising New Contrast Material for Computed Tomography of the Spleen", Radiology 140:507–511, Aug., 1981.

Ryan et al, "The Preparation and Characterization of Liposomes Containing X-ray Contrast Agents", Biochemica et Biophysica Acta. 756 (1983), 106–110 (Elsevier Biomedical Press).

*Primary Examiner*—Glennon H. Hollrah
*Assistant Examiner*—Raymond Covington
*Attorney, Agent, or Firm*—Lawrence S. Levinson; Burton Rodney

[57] ABSTRACT

New X-ray contrast agents are provided which are alkylammonium complexes of diatrizoic acid having the structure

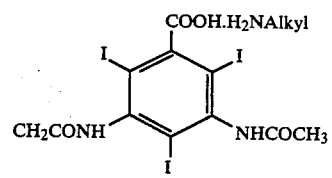

X-ray contrast medium containing the above X-ray contrast agent and a carrier therefor such as a liposome carrier, and a method for the X-ray visualization of body cavities and organs are also provided.

15 Claims, No Drawings

ALKYLAMMONIUM COMPLEXES OF DIATRIZOIC ACID AS X-RAY CONTRAST AGENTS

FIELD OF THE INVENTION

The present invention relates to alkylammonium complexes of diatrizoic acid which are useful as contrast agents, to X-ray contrast media containing such contrast agents, which may include a liposome carrier, and to a method of using the above X-ray contrast media in the X-ray visualization of body cavities and organs.

BACKGROUND OF THE INVENTION

The use of certain iodine-containing benzoic acid derivatives as X-ray contrast agents is well known. For example, U.S. Pat. No. 4,018,783 to Soulal discloses X-ray contrast agents which are of the structure

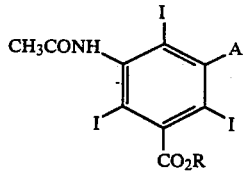

wherein A is $-CONHCH_3$ or $-N(CH_3)COCH_3$ and R is a phthalide group or lower alkyl optionally substituted with an aryl or dialkylamino group, or with a group of the formula

wherein $R_1$ is lower alkyl, except that when A is $-CONHCH_3$, then R is not acetoxymethyl or pivaloyloxymethyl.

British Pat. No. 866,184 discloses triiodobenzoic acid derivatives of the structure

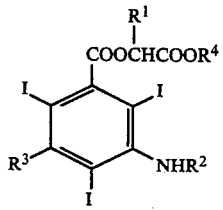

wherein $R^1$ is H or lower alkyl; $R^2$ is H or lower alkanoyl; $R^3$ is H or lower alkanoylamino.

U.S. Pat. No. 3,128,301 discloses 3,5-diacylamino-2,4,6-triiodobenzoic acid esters of the structure

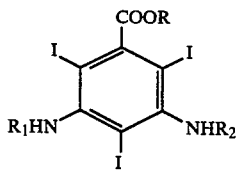

wherein R is lower alkyl, and $R_1$ and $R_2$ are lower alkanoyl.

U.S. Pat. No. 4,192,859 to Mackaness et al discloses the use of liposomes as carriers for contrast agents such as diatrizoic acid, sodium diatrizoate and other iodinated contrast agents.

Havron et al in "Radiopaque Liposomes: A Promising New Contrast Material for Computed Tomography of the Spleen", Radiology 140: 507–511, August, 1981, disclose radiopaque positively charged liposomes as carriers for diatrizoate meglumine and diatrizoate sodium (Renografin) for use in computed tomography of the spleen.

Ryan et al in "The Preparation and Characterization of Liposomes Containing X-Ray Contrast Agents," Biochemica et Biophysica Acta. 756 (1983), 106–110 (Elsevier Biomedical Press) disclose use of Renografin and Hypaque in liposomes in X-ray computed tomography.

DESCRIPTION OF THE INVENTION

In accordance with the present invention, new X-ray contrast agents are provided having the formula I

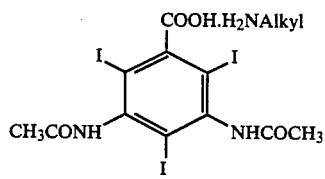

wherein alkyl contains 10 to 22 carbons and preferably 14 to 20 carbons.

Further in accordance with the present invention, there is provided an X-ray contrast medium or composition which includes a compound of formula I alone or together with the sodium salt of diatrizoic acid and/or the N-methylglucamine salt of diatrizoic acid, (for example, Renografin, trademark of E. R. Squibb & Sons, Inc.), together with a suitable pharmaceutically acceptable carrier therefor, which carrier may comprise a liposome or other conventional carrier.

The term "alkyl" as employed herein includes both straight and branched chain radicals of 10 to 22 carbons, preferably 14 to 20 carbons, such as, decyl, undecyl, dodecyl, tridecyl, tetradecyl, pentadecyl, hexadecyl, septadecyl, octadecyl, nonadecyl, eicosanyl, heneicosanyl, and docosanyl, and including the various branched chain-isomers thereof.

The X-ray contrast agents of the invention may be prepared by forming a solution of diatrizoic acid A in an inert organic solvent

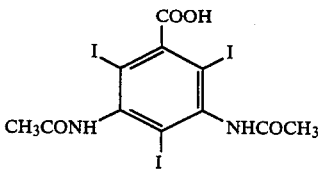

such as acetone, methanol or ethanol, or mixtures thereof, forming a solution of the appropriate alkylamine B

in an appropriate inert organic solvent, such as methanol, chloroform, acetone, or mixtures thereof in the case of stearylamine, mixing the solutions of diatrizoic acid and alkylamine, and then removing the solvent to yield the alkylammonium complex of diatrizoic acid of formula I.

The X-ray contrast medium of the invention which includes an X-ray contrast agent of the invention and a pharmaceutically acceptable carrier therefor may be used in X-raying and scanning body cavities and organs.

In a preferred embodiment of the invention, an X-ray contrast agent of formula I of the invention alone or in combination with one or more salts of diatrizoic acid, such as the sodium salt and/or N-methylglucamine salt, are incorporated in a pharmaceutically acceptable carrier. In a more preferred embodiment of the invention, the X-ray contrast agent of formula I alone or in combination with one or more salts of diatrizoic acid (as described above) is incorporated in a liposome carrier employing procedures as described in U.S. Pat. No. 4,192,859 and as such is especially useful in lymphographic techniques. The X-ray contrast agent of the invention may be employed in a weight ratio to one or a mixture of sodium salt and/or N-methylglucamine salt of diatrizoic acid of within the range of from about 0.1:1 to about 100:1 and preferably from about 1:1 to about 10:1. The sodium salt of diatrizoic acid and the N-methylglucamine salt of diatrizoic acid may be employed in a weight ratio to each other (sodium salt:N-methyl glucamine salt) of within the range of from about 0.1:1 to about 100:1 and preferably from about 1:1 to about 10:1.

The X-ray contrast agent, whether the alkylammonium complex of diatrizoic acid alone or in admixture with the sodium and/or N-methylglucamine salts of diatrizoic acid, will be present in the liposome contrast medium in an amount within the range of from about 20 to about 60% by weight of the contrast medium, and preferably from about 30 to about 50% by weight of the contrast medium, depending upon the desired concentration of iodine.

The liposomes and preparations for same suitable for use herein include those disclosed in U.S. Pat. No. 3,957,971 to Oleniacz; G. Sessa et al, J. Lipid Res., Vol. 9, 310 (1968), as well as in the various references discussed hereinbefore, and other liposomes known in the art.

Liposomes employed in the present invention generally comprise lipid materials, predominantly of the phospholipid type (for example, a sterol), lecithin, dicetyl phosphate, or stearylamine, in an organic solvent.

When employing an X-ray contrast medium containing an X-ray contrast agent and a liposome carrier therefor, according to the invention, the X-ray contrast medium is administered to the body of the test object whereafter the body is exposed to X-rays and photographs may be taken or the image observed directly on a fluorescent screen, or other X-ray techniques may be applied in a conventional manner. The dose of contrast medium administered is selected according to the category of the investigation, so that a sufficient contrast effect is obtained.

The test object may include mammalian species, such as humans, dogs, cats, monkeys, sheep, pigs, horses, bovine animals and the like.

As indicated, the X-ray contrast medium of the invention is particularly suitable for use in lymphography. However, the X-ray contrast medium may be employed for visualizing many different body cavities and organs, such as the chest cavity including the bronchial tree, and the gastrointestinal tract. In the latter instance, the contrast medium is administered perorally as a thick liposomal formulation. The intestines can also be visualized by administering the X-ray contrast medium rectally in the form of a liposomal enema. Another example is the visualization of blood vessels subsequent to the X-ray contrast medium being injected in the form of a sterile liposomal preparation. When injected intraveneously the X-ray contrast medium is excreted with the urine and enables visibilization of the renal pelvis, ureters and bladders. Further examples are the use of the X-ray contrast media in imaging the biliary system, hysterosalpingography, cholangiography, myelography, angiography, sialography, and liver and spleen imaging.

As indicated, the X-ray contrast agent of the invention may be combined with a pharmaceutically acceptable carrier (other than liposomes) depending upon the particular use of the final composition which may be employed for diagnostic purposes in bronchography, the delineation of tissue planes, salpinography and transumbilical heptography. In such applications, the X-ray contrast agents of the invention may be administered as an aqueous dispersion, an aerosol, in microencapsulated form or in an oily solution. Thus, for bronchography, the X-ray contrast agent of the invention may be combined with a non-toxic water-insoluble or metabolizable solid carrier, such as lactose, for purpose of insufflation.

The following Examples represent preferred embodiments of the present invention.

EXAMPLE 1

Diatrizoic acid (1.0 g) was dissolved in a mixture of acetone and methanol (1:1, approximately 50 ml). Stearylamine (0.44 g) was dissolved in a mixture of methanol and chloroform (1:3, approximately 50 ml). The two solutions were mixed by shaking for 2 minutes, and the mixture was then evaporated under reduced pressure using a rotary evaporator to yield the title compound in the form of white crystalline solid, m.p. 282° C. (decomp), slighty soluble in chloroform, very soluble in methanol/chloroform (1:3), insoluble in water, 1% aqueous sodium carbonate solution, acetone, and acetone/methanol (1:1).

EXAMPLE 2

Nonadecyl Ammonium Complex of Diatrizoic Acid

Following the procedure of Example 1 except substituting nonadecylamine for stearylamine, the title compound is obtained.

EXAMPLE 3

Septadecyl Ammonium Complex of Diatrizoic Acid

Following the procedure of Example 1 except substituting septadecylamine for stearylamine, the title compound is obtained.

EXAMPLE 4

Pentadecyl Ammonium Complex of Diatrizoic Acid

Following the procedure of Example 1 except substituting pentadecylamine for stearylamine, the title compound is obtained.

EXAMPLE 5

Dodecyl Ammonium Complex of Diatrizoic Acid

Following the procedure of Example 1 except substituting dodecylamine for stearylamine, the title compound is obtained.

EXAMPLE 6

Eicosanylammonium Complex of Diatrizoic Acid

Following the procedure of Example 1 except substituting eicosanylamine for stearylamine, the title compound is obtained.

EXAMPLE 7

A quantity of each of 1.4 g egg lecithin (egg phosphotidyl choline) and 0.6 g of cholesterol are dissolved in 20 ml of chloroform. The chloroform is evaporated leaving a film of neutral phospholipid residue. Two grams of the phospholipid is then added to 7 ml of neutral buffered solution containing 4 g of the X-ray contrast agent stearyl ammonium complex of diatrizoic acid prepared as described in Example 1. The mixture is stirred with a magnetic stirrer until a final homogeneous liposomal mixture is obtained. Ten milliliters of the final liposome preparation contains 4 g of the X-ray contrast agent.

The so-formed X-ray contrast medium may be employed as described in U.S. Pat. No. 4,192,859.

EXAMPLE 8

Two grams of neutral phospholipid residue, prepared as described in Example 7, is added to 6.7 ml of neutral buffered solution containing 4 g of stearylammonium complex of diatrizoic acid. The mixture is stirred with a magnetic stirrer until a homogeneous liposomal mixture is obtained.

The so-formed contrast medium may be employed as described in U.S. Pat. No. 4,182,859.

EXAMPLE 9

An X-ray contrast composition is prepared by admixing stearylammonium complex of diatrizoic acid (10 g) and lactose (0.5 g).

EXAMPLE 10

Two grams of neutral phospholipid residue, prepared as described in Example 7, is added to 6.7 ml of neutral buffered solution containing 4 g of stearylammonium complex of diatrizoic acid, and 2 g of sodium diatrizoate. The mixture is stirred with a magnetic stirrer until a homogeneous liposomal mixture is obtained.

The so-formed contrast medium may be employed as described in U.S. Pat. No. 4,182,859.

EXAMPLE 11

Two grams of neutral phospholipid residue, prepared as described in Example 7, is added to 6.7 ml of neutral buffered solution containing 4 g of stearylammonium complex of diatrizoic acid and 2 g N-methylglucoamine salt of diatrizoic acid. The mixture is stirred with a magnetic stirrer until a homogeneous liposomal mixture is obtained.

The so-formed contrast medium may be employed as described in U.S. Pat. No. 4,182,859.

What is claimed is:

1. An X-ray contrast agent having the structure

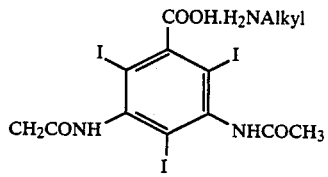

wherein alkyl contains 10 to 22 carbons.

2. The compound as defined in claim 1 wherein alkyl contains 14 to 20 carbons.

3. The compound as defined in claim 2 wherein alkyl as $C_{18}H_{37}$.

4. An X-ray contrast medium comprising an X-ray contrast agent as defined in claim 1 and a carrier therefor.

5. The X-ray contrast medium as defined in claim 4 wherein said contrast agent is the stearylammonium complex of diatrizoic acid.

6. The X-ray contrast medium as defined in claim 5 wherein said carrier is a liposome.

7. The X-ray contrast medium as defined in claim 6 wherein said contrast agent is employed together with sodium diatrizoate and/or the N-methylglucamine salt of diatrizoic acid.

8. A method for the X-ray visualization of body cavities and organs, which comprises administering to the body of the test object an effective contrast producing amount of an X-ray contrast medium as defined in claim 4.

9. The method as defined in claim 8 wherein the liver is visualized.

10. The method as defined in claim 8 wherein the spleen is visualized.

11. The method as defined in claim 8 wherein the gall bladder is visualized.

12. The method as defined in claim 8 wherein the spinal cord is visualized.

13. The method as defined in claim 8 wherein the X-ray contrast agent employed is the stearylammonium complex diatrizoic acid.

14. The method for X-ray visualization of lymphatic channels, which comprises administering to the body of the test object a contrast producing amount of an X-ray contrast medium as defined in claim 6.

15. A method for the radiographic examination of the gastrointestinal tract, which comprises administering to the body of the test object an effective contrast producing amount of an X-ray contrast medium as define in claim 4.

* * * * *

UNITED STATES PATENT AND TRADEMARK OFFICE
CERTIFICATE OF CORRECTION

PATENT NO. : 4,735,795
DATED : April 5, 1988
INVENTOR(S) : Malcolm L. Robinson et al.

It is certified that error appears in the above-identified patent and that said Letters Patent is hereby corrected as shown below:

Column 6, Claim 1, the structure should read

-- 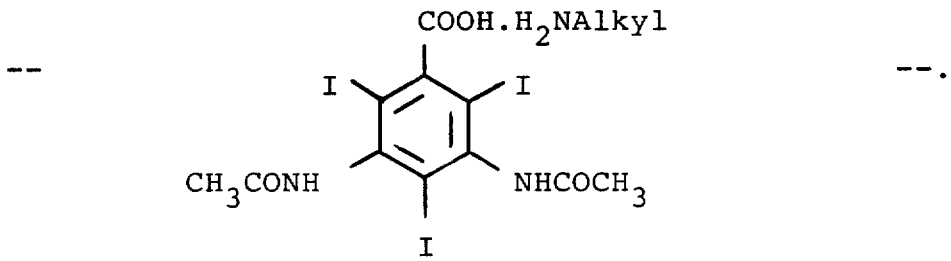 --.

Signed and Sealed this

Second Day of August, 1988

*Attest:*

DONALD J. QUIGG

*Attesting Officer*  Commissioner of Patents and Trademarks